(12) United States Patent
Farris

(10) Patent No.: US 8,579,949 B2
(45) Date of Patent: Nov. 12, 2013

(54) PROVISIONAL FIXATION FOR A MULTI-AXIAL SCREW ASSEMBLY

(75) Inventor: Robert A Farris, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 232 days.

(21) Appl. No.: 13/016,699

(22) Filed: Jan. 28, 2011

(65) Prior Publication Data

US 2012/0197314 A1    Aug. 2, 2012

(51) Int. Cl.
*A61B 17/84*    (2006.01)

(52) U.S. Cl.
USPC ........................................... 606/308; 606/305

(58) Field of Classification Search
USPC ......... 606/264–275, 300–301, 305–308, 325; 411/197, 204, 213, 314, 371.2–372, 411/533, 943
See application file for complete search history.

(56) References Cited

U.S. PATENT DOCUMENTS

| | | | |
|---|---|---|---|
| 2005/0080420 A1* | 4/2005 | Farris et al. ...................... | 606/61 |
| 2006/0084978 A1* | 4/2006 | Mokhtar ......................... | 606/61 |
| 2006/0149232 A1* | 7/2006 | Sasing ............................ | 606/61 |
| 2010/0125302 A1* | 5/2010 | Hammill et al. ............... | 606/308 |
| 2010/0131018 A1* | 5/2010 | Konieczynski et al. ....... | 606/308 |

* cited by examiner

*Primary Examiner* — Todd Manahan
*Assistant Examiner* — Eric S Gibson

(57) ABSTRACT

A multi-axial screw assembly comprises a receiver, a base member, a crown and a bone screw. The base member includes an aperture extending through the base member and an opening on a bottom portion of the base member. The base member is rotatable relative to the receiver and has an inner wall extending partially around the aperture. The crown is received in the receiver and configured to mate to the base member. The crown has a projection configured to extend into the opening of the base member. The projection is configured to have an abutting surface. The bone screw is located between the base member and the crown, the bone screw is configured to be provisionally fixed within the receiver by a force between the abutting surface of the projection and the inner wall of the base member.

15 Claims, 4 Drawing Sheets

PROVISIONAL FIXATION FOR A MULTI-AXIAL SCREW ASSEMBLY

FIELD OF INVENTION

Embodiments of the invention relate to implants used for correction of orthopedic injuries or deformities, and more specifically, but not exclusively, relate to multi-axial screws implanted in bone for stabilizing longitudinal support members.

BACKGROUND

Typical implant systems include several pieces, which may be associated or useful with only specific other pieces. Among such pieces are screws, hooks rods, plates and similar longitudinal members for supporting, holding and/or correcting one or more bones. Such longitudinal members can be fastened to bones via direct or indirect connection to hooks, screws, bolts or other fasteners, and may be linked to each other by a variety of connectors. In the spinal field, for example, screws or other fasteners can be attached to two or more vertebrae, the vertebrae can be adjusted into their normal or a therapeutically better position, and longitudinal members are connected to the fasteners so that the vertebrae are held in the normal or therapeutically improved position.

Accordingly, known bone screws, hooks, clamps and other bone fasteners or fixation devices can be connected or adjoined to a particular bone or bones as a connection between the remainder of the implant and the bone(s). Where a rod is used as a support and stabilizing member, commonly a series of two or more screws are inserted into two or more vertebrae to be instrumented. A rod is then placed within or coupled to the heads of the screws, or is placed within a connecting device that links the rod and a screw head, and the connections are tightened. In this way, a rigid supporting structure is fixed to the vertebrae, with the rod providing the support that maintains and/or promotes correction of the vertebral malformation or injury.

Some devices allow one or more degrees of freedom between a fastening portion or fastening member and a receiving portion or member, reducing the required precision of placement of the fixation device, since a head portion of the fixation device is multi-axially positionable around the bone-threaded or hook portion. The head can thus be positioned so as to easily receive the rod, limiting or removing much of the positioning difficulty inherent in prior devices. However, such multi-angle positioning between the fastening portion and the receiving portion for every relative orientation of those parts may create difficulty in orienting the parts during surgery.

The description herein of problems and disadvantages of known apparatuses, methods, and devices is not intended to limit the invention to the exclusion of these known entities. Indeed, embodiments of the invention may include, as a part of the embodiment, portions or all of one or more of the known apparatus, methods, and devices without suffering from the disadvantages and problems noted herein.

SUMMARY OF THE INVENTION

An aspect of the invention may include a multi-axial screw assembly comprising a receiver, a base member, a crown and a bone screw. The receiver includes a channel for receiving a rod and an aperture extending from a bottom portion of the receiver. The base member includes an aperture extending through the base member and an opening on a bottom portion of the base member. The base member is configured to couple to the receiver such that the aperture of the receiver is generally aligned with the aperture of the base member. The base member is rotatable relative to the receiver and has an inner wall extending partially around the aperture. The crown is received in the receiver and configured to mate to the base member. The crown has a projection configured to extend into the opening of the base member. The projection is configured to have an abutting surface. The bone screw is located between the base member and the crown, the bone screw is configured to be provisionally fixed within the receiver by a force between the abutting surface of the projection and the inner wall of the base member.

Another aspect of the invention may include a method of forming a crown for a multi-axial screw assembly. A step provides machining an undersurface of the crown. The undersurface has a generally uniform radius of curvature. Another step provides machining an abutting surface of a projection extending from the crown. The abutting surface has a radius of curvature generally equal to the radius of curvature of the undersurface of the crown. The center of the radius of curvature of the abutting surface is offset from the center of the radius of curvature of the undersurface.

Additional aspects and features of the present disclosure will be apparent from the detailed description and claims as set forth below.

DETAILED DESCRIPTION

Figure 1:
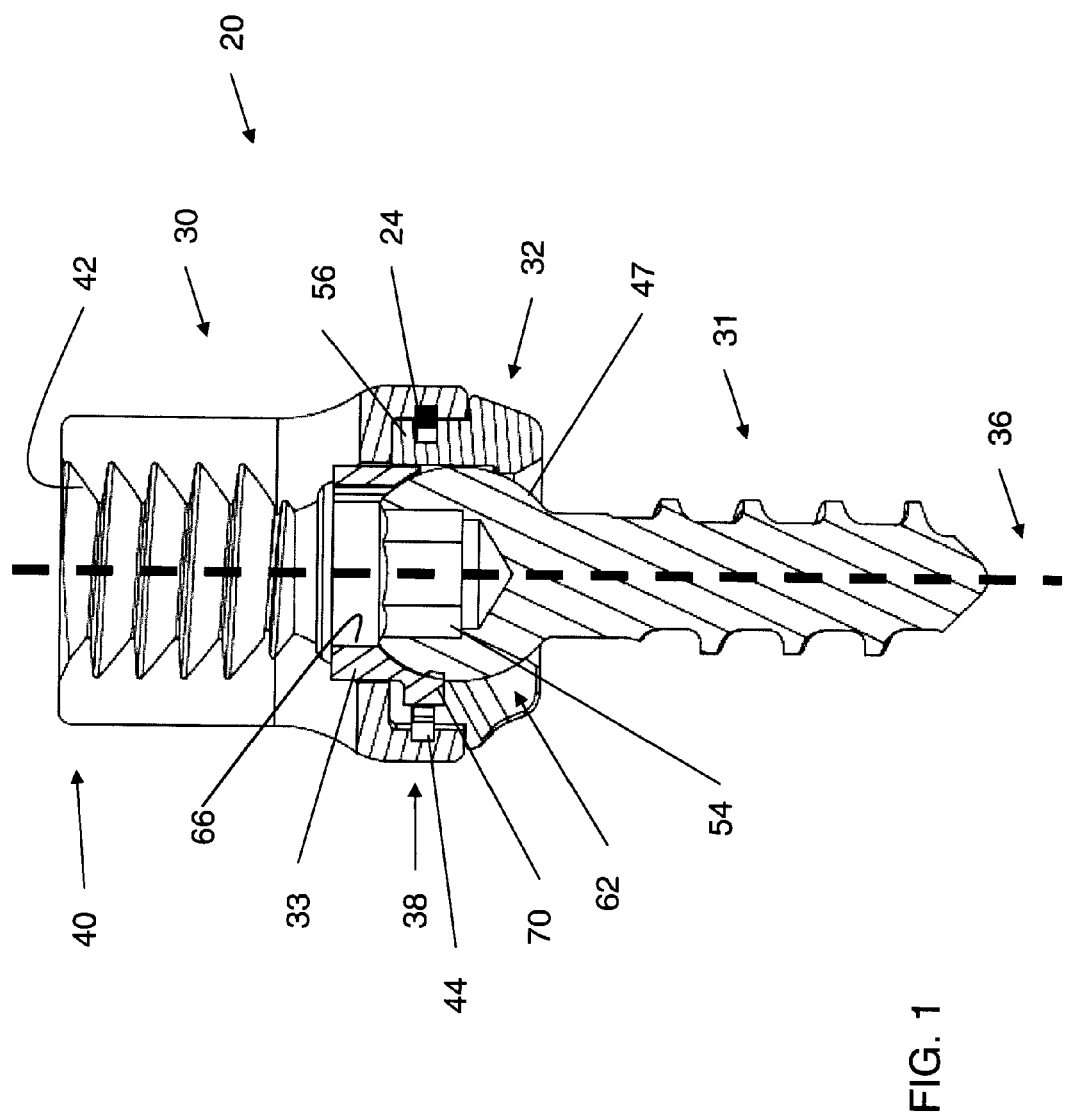
FIG. 1 is a cross sectional view of a multi-axial screw according to an aspect of the invention.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

FIG. 1 is a cross sectional view of a multi-axial screw according to an aspect of the invention. Multi-axial screw assembly 20 includes a snap ring 24, a receiver 30, a bone anchoring member 31, a base or retaining member 32, and a crown 33. The assembly 20 is configured such that a head portion 47 of the bone anchoring member 31 is captured between the receiver 30 and the base member 32 along a central axis 36 of the assembly 20. Receiver 30 is also configured to accommodate a rod or other longitudinal member through an aperture generally perpendicular to the bone anchoring member 31 when the bone anchoring member 31 is vertically seated in the receiver 30. In a specific embodiment, the receiver 30 includes a lower portion 38 and a top portion 40, a threaded portion 42 at or near top portion 40 receives a compression member (for example, a set screw or other element with external threads) to capture the rod within the receiver 30. Threaded portion 42 could be outside of receiver 30 if an external compression member is used. Alternatively, receiver 30 could be externally and/or internally configured for compression members using snapping, twisting or other types of closures. The lower portion 38 of receiver 30 has a groove 44. In the illustrated embodiment, groove 44 extends around an aperture in the receiver 30 around the central axis 36.

Base or retaining member 32 in the embodiment shown in FIG. 1 is substantially circular in one embodiment. A flange 56 captures the retaining member 32 in the receiving member 30 via the snap ring 24. Base member 32 includes an opening 62 around its circumference. The opening 62 allows the head portion 47 of bone anchoring member 31 to rotate with respect to base member 32, allowing positioning of bone anchoring member 31 at any of a variety of angles with respect to central axis 36 of receiver 30. The opening 62 in base member 32 includes a cutout portion (which may be a slot extending through the base member 32) to allow for increased angulation in a specific direction as the bone anchoring member 31 rotates relative to the receiver 30.

The base member 32 can be rotated with respect to the receiver 30. This allows the opening 62 of the base member to be rotationally oriented with respect to the receiver 30. The maximum angle, then, achieved through the opening 62 of the base may be achieved at any relative orientation to the receiver 30 by rotating the base 32 relative to the receiver 30 to the proper position.

Crown 33 includes an internal aperture 66, an undersurface 68 (FIG. 4), and a projection 70. Crown 33 is sized to fit within receiver 30 so that crown 33 has some freedom of axial movement along the central axis 36. Internal aperture 66 is provided to allow access to a tool receiving feature 54 in bone anchoring member 31 when crown 33 is above or atop bone anchoring member 31. Undersurface 68 is preferably configured to accommodate at least a part of head portion 47 of bone anchoring member 31. For example, undersurface 68 may be shaped (e.g. spherical, rounded, conical, or otherwise) to allow relative movement between crown 33 and part or all of head portion 47 of bone anchoring member 31. In the embodiment in which both undersurface 68 and head portion 47 have a rounded or spherical portion, undersurface 68 may have substantially the same or greater diameter as head portion 47.

The projection 70 extends from the crown member 33 generally along the axis 36 of the assembly 20. The projection 70 may extend into the opening 62 of the base member 32. The projection 70 exerts a force on the head portion 47 of the bone anchoring member 31. A resultant force oriented opposite that force is exerted by the base member 32 on the bone anchoring member 31. Motion of the receiver 30 relative to the bone anchoring member 31 is constrained. The motion is constrained by the frictional forces between the contacting surfaces of the projection 70, the head portion 47, and the base member 32. Friction between the head portion 47 and the projection and friction between the head portion 47 and the base member 32 is proportional to the force exerted by the projection 70 onto the head portion 47.

Snap ring 24 is received between the base 32 and the receiver 30. The snap ring axially fixes the base 32 to the receiver 30 while allowing relative rotation between these parts 30 and 32. The snap ring 24 is received under the flange 56 of the base 32. The snap ring 24, when it expands, sits under the flange 56 in the groove 44 inside the receiver 30 (FIG. 2).

Figure 2:
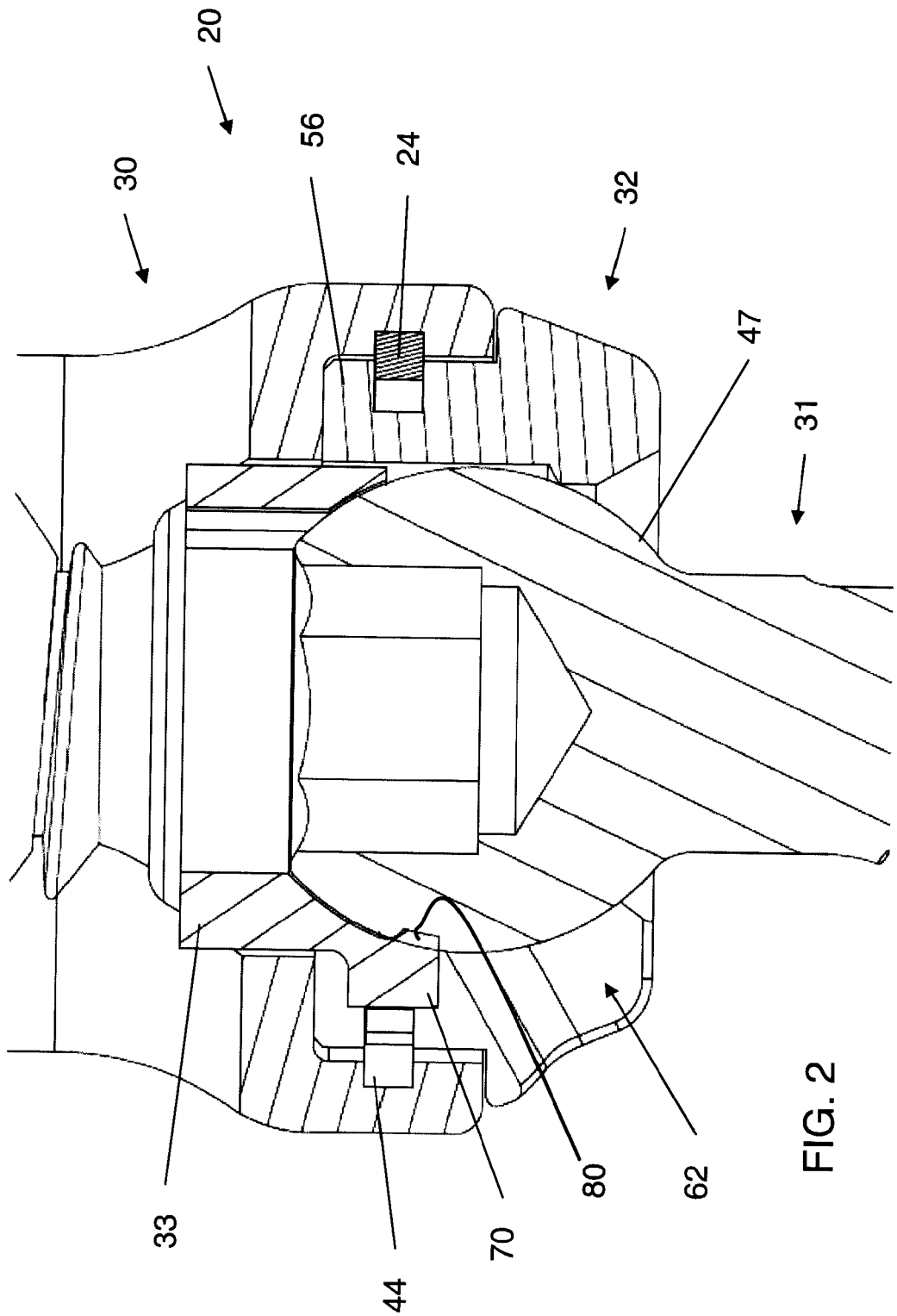
FIG. 2 is a magnified view of the embodiment of FIG. 1.

FIG. 2 is a magnified view of the embodiment of FIG. 1. The projection 70 includes an abutting surface 80. The abutting surface 80 abuts the head portion 47 of the bone anchoring member 31. The projection 70 may flex outward within the opening 62 when the head portion 47 of the bone anchoring member 31 is fixed into the base member 32. The crown 33 is generally laterally fixed within the receiver 30 so that it may not laterally move within the receiver 30. The projection 70, projecting into the opening 62, may flex outward slightly as it abuts the head portion 47 while the crown 33 remains within the receiver 30.

Figure 3:
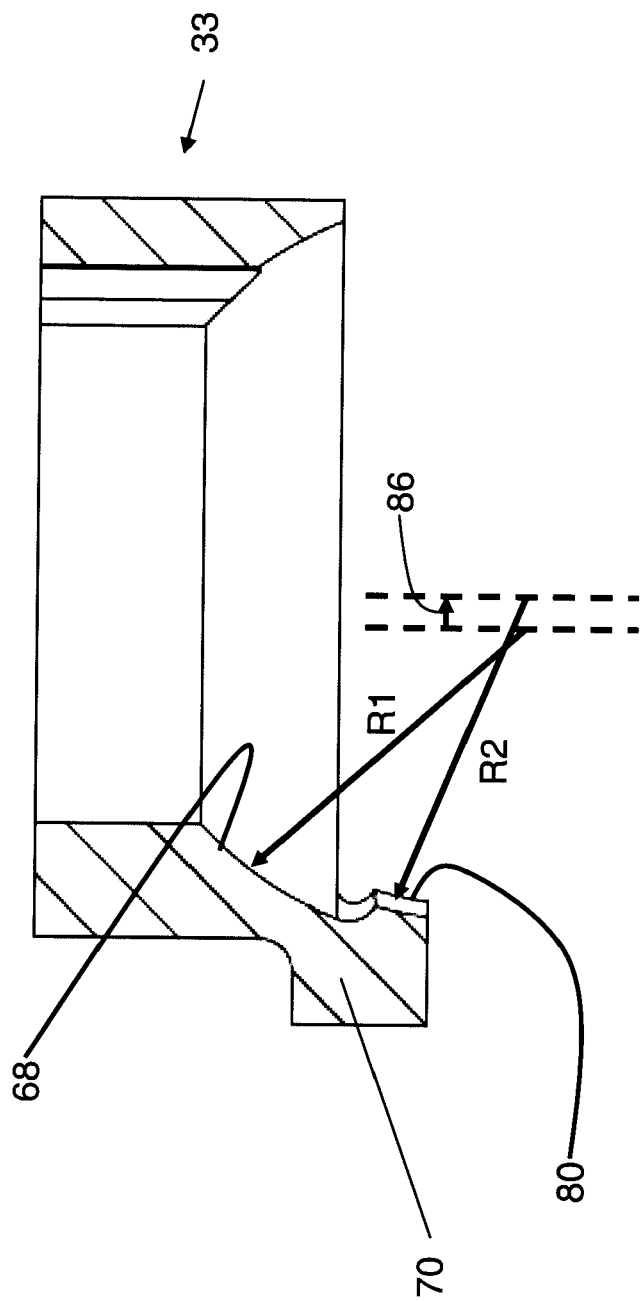
FIG. 3 is a cross sectional view of a crown according to the embodiment of FIG. 1.

FIG. 3 is a cross sectional view of the crown 33 according to the embodiment of FIG. 1. The undersurface 68 of the crown 33 is machined with a spherical tool having a radius $R_1$. The undersurface 68 machining procedure does not machine the surface 80 of the projection 70. The projection 70 is machined with a tool having the same radius $R_1$, except the center point of the radius of the tool is offset by an offset distance 86. The offset distance (moved away from the surface 80 of the projection 70) makes the abutting surface 80 of the projection 70 proud relative to the spherical surface of the undersurface. The offset 86, while shown here as a lateral offset, may be an offset in other directions. For example, the offset may be a vertical offset, or may be a combination of a vertical and lateral offset. Each of these machining processes will result in an abutting surface 70 proud relative to the undersurface 68 of the crown 33.

The abutting surface 80 may be machined with a tool that may machine a spherical surface (like the cutting surface of the tool that may machine the undersurface 68) or may be another shape having a cutting radius equal to the cutting radius of the tool for machining the undersurface 68. For example, the abutting surface 80 may be machined to a cylindrical surface instead of a spherical surface. By using a similarly radiused machining process, the abutting surface 80 may increase contact area with the surface of the head portion 47 of the bone anchoring member 31.

Figure 4:
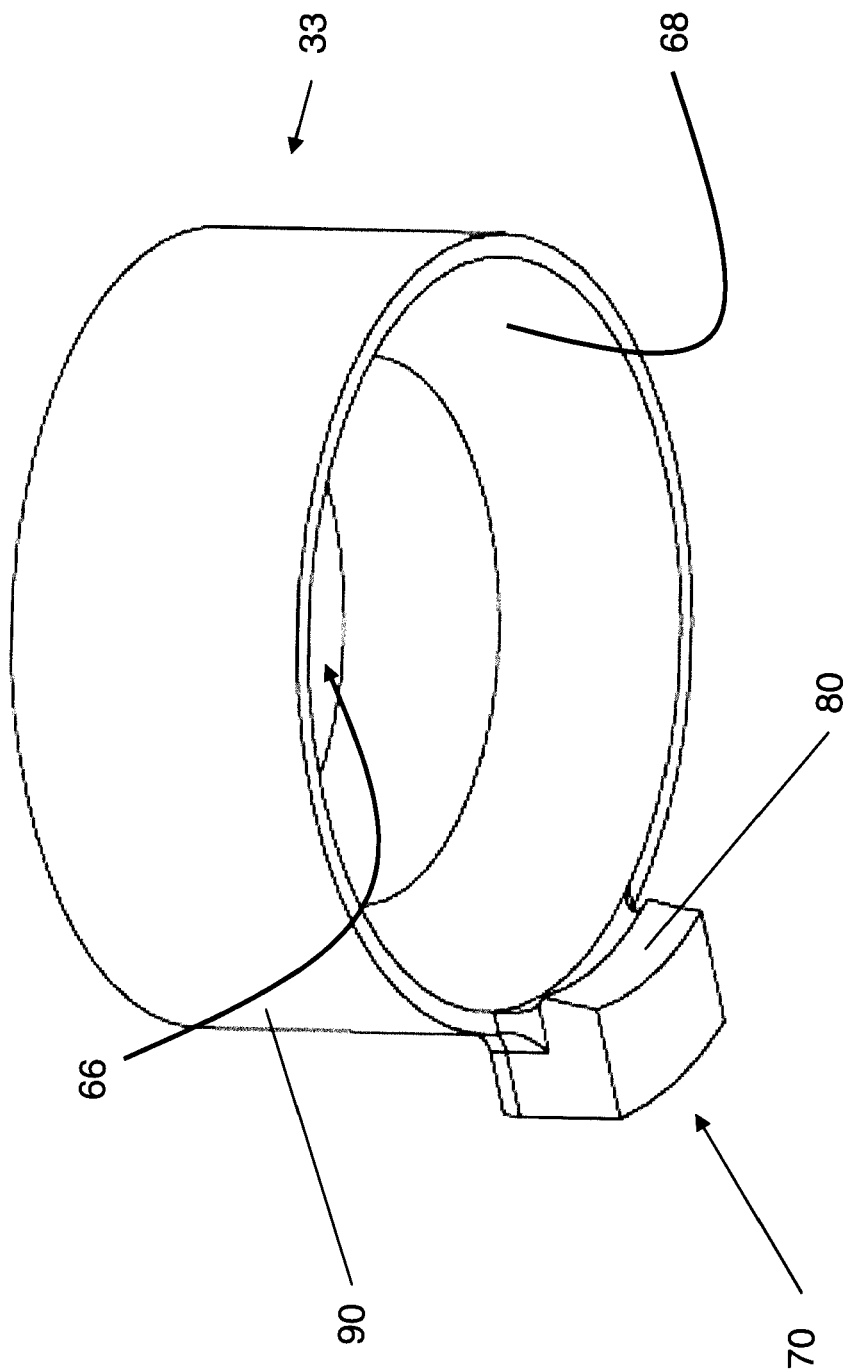
FIG. 4 is a perspective bottom view of the crown of FIG. 3.

FIG. 4 is a perspective bottom view of the crown of FIG. 3. The abutting surface 80 of the projection 70 extends into an aperture defined by the undersurface 68 of the crown 33. The undersurface 68 of the crown 33, preferably having a radius generally equal to the radius of the head portion of the bone screw, opens the aperture wider at a bottom portion of the crown 33. The projection 70 extending from the crown 33 may extend outward beyond an outer surface 90 of the crown 33. The projection 70 extends into the opening on the base member. The thickness of the projection 70 (both into the aperture and away from the aperture) may control the flexibility (and thus the resistive force) of the projection 70 against the head portion of the bone anchoring member. Additionally, the width, depth and height of the projection 70, as well as the surface finish and shape of the projection 70 may also control the force exerted on the head portion of the bone anchoring member.

The foregoing detailed description is provided to describe the invention in detail, and is not intended to limit the invention. Those skilled in the art will appreciate that various modifications may be made to the invention without departing significantly from the spirit and scope thereof.

Furthermore, it is understood that all spatial references, such as "first," "second," "exterior," "interior," "superior," "inferior," "anterior," "posterior," "central," "annular," "outer," and "inner," are for illustrative purposes only and can be varied within the scope of the disclosure.

The invention claimed is:

1. A multi-axial screw assembly, comprising:
 a receiver comprising a channel for receiving a rod and an aperture extending from a bottom portion of the receiver;
 a base member comprising an aperture extending through the base member and an opening on a bottom portion of the base member, the base member configured to couple to the receiver such that the aperture of the receiver is generally aligned with the aperture of the base member, the base member being rotatable relative to the receiver, the base member having an inner wall extending partially around the aperture of the base member;

a crown received in the receiver configured to mate to the base member, the crown having a projection configured to extend into the opening of the base member, the projection comprising an abutting surface offset from an undersurface of the crown such that the abutting surface is proud relative to the undersurface; and a bone screw located between the base member and the crown, the bone screw configured to be provisionally fixed within the receiver by a force between the abutting surface of the projection and the inner wall of the base member, wherein the projection is configured to flex outwardly, narrowing the offset, until a portion of the bone screw is in flush contact with the undersurface when the bone screw is positioned between the base member and the crown.

2. The multi-axial screw assembly of claim 1, wherein the abutting surface extends from a side wall of the crown.

3. The multi-axial screw assembly of claim 2, wherein the abutting surface is formed using a spherical cutting tool.

4. The multi-axial screw assembly of claim 1, further comprising a snap ring received between the base member and the receiver, axially fixing the base member to the receiver.

5. The multi-axial screw assembly of claim 4, wherein a lower portion of the receiver includes a groove configured for disposal of the snap ring and the base member includes a flange that the snap ring sits under.

6. The multi-axial screw assembly of claim 4, wherein an inner surface of the snap ring engages the projection while an outer surface of the snap ring engages the receiver.

7. The multi-axial screw assembly of claim 1, wherein the abutting surface has a radius of curvature generally equal to that of the undersurface.

8. The multi-axial screw assembly of claim 1, wherein the abutting surface has a radius of curvature greater than that of the undersurface.

9. The multi-axial screw assembly of claim 1, wherein the abutting surface is concavely curved.

10. The multi-axial screw assembly of claim 1, wherein the abutting surface has an arcuate configuration.

11. The multi-axial screw assembly of claim 1, wherein an interface between the undersurface and the abutting surface defines an edge, a distance between the edge and an outer surface of the projection being greater than a distance between the abutting surface and the outer surface of the projection.

12. The multi-axial screw assembly of claim 1, wherein the opening in the base member includes a slot defining a cutout portion configured to allow for increased angulation in a specific direction as the bone screw rotates relative to the receiver.

13. The multi-axial screw assembly of claim 1, wherein a body of the crown has a cylindrical configuration, the projection extending from an outer surface of the body in a direction that is perpendicular to an axis defined by the crown.

14. A multi-axial screw assembly, comprising:

a receiver comprising an inner surface defining a first aperture, the inner surface comprising a groove extending into the inner surface;

a base member disposed in the first aperture, the base member comprising an inner surface defining a second aperture, the base member comprising an outer surface including a pair of spaced apart flanges defining a gap therebetween that is aligned with the groove, the outer surface defining a ledge, a bottom surface of the receiver engaging the ledge;

a crown comprising a body having a cylindrical configuration disposed in the apertures, the body being bisected axially into first and second sections, the first section comprising a projection extending from an outer surface of the base member, the projection comprising an abutting surface offset from an undersurface of the crown such that the abutting surface is proud relative to the undersurface, the second section being free of projections extending from the body;

a snap ring positioned in the groove and the gap such that an inner surface of the snap ring engages an outer surface of the projection; and a bone screw positioned within the apertures such that a head of the bone screw engages the undersurface and the abutting surface.

15. The multi-axial screw assembly of claim 14, wherein the abutting surface has a radius of curvature generally equal to that of the undersurface.

* * * * *